United States Patent [19]

Kelly et al.

[11] Patent Number: 4,639,252
[45] Date of Patent: Jan. 27, 1987

[54] VENOUS RETURN CATHETER

[75] Inventors: Michael N. Kelly, Salt Lake City, Utah; John B. Foster, Rolling Hills Estates; Robert D. Foster, San Pedro, both of Calif.

[73] Assignee: Research Medical, Inc., Salt Lake City, Utah

[21] Appl. No.: 720,172

[22] Filed: Apr. 5, 1985

[51] Int. Cl.$^4$ ............................................. A61M 25/00
[52] U.S. Cl. ......................................... 604/282; 604/4
[58] Field of Search .............................. 604/282, 4-6, 604/43, 93

[56] References Cited

U.S. PATENT DOCUMENTS

| | | | |
|---|---|---|---|
| 2,211,975 | 8/1940 | Hendrickson | 604/282 |
| 2,269,823 | 1/1942 | Kreiselman | 128/84 |
| 3,416,531 | 12/1968 | Edwards | 604/282 |
| 3,426,744 | 2/1969 | Ball | 604/282 X |
| 3,684,604 | 8/1972 | Zwart | 604/282 |
| 3,851,646 | 12/1974 | Sarns | 128/214 |
| 4,011,869 | 3/1977 | Seiler, Jr. | 128/276 |
| 4,037,599 | 7/1977 | Raulerson | 128/214 |
| 4,129,129 | 12/1978 | Amrine | 128/214 |
| 4,493,696 | 1/1985 | Uldall | 604/43 |

OTHER PUBLICATIONS

Page from catalog of U.S.C.I. illustrating that compan's 1969 type venous return cannula intended for use when single venous drainage from the right atrium and inferior vena cava is desired.
Maraist, "Coronary Blood Flow as Measured Directly Within the Caval Venous Return Shunted Past the Right Heart," 31, *Experimental Cardiac Surgery*, 146, (1952).
Lam, "Experiences in the Use of Cardioplegia (Induced Cardiac Arrest) in the Repair of Interventricular Septal Defects," 34, *Journal of Thoracic Surgery*, 509, (1957).
Cooley, "Surgical Consideration in Repair of Ventricular and Atrial Septal Defects Utilizing Cardiopulmonary Bypass," 43, *Surgery*, 214, (1958).
Harshbarger, "Studies in Extracorporeal Circulation: Surgical Techniques," 106, *Surgery, Gynecology & Obstetrics*, 111 (1958).
Blanco, "Single Catheter Gravity Drainage of the Right Atrium or Right Ventricle During Total Cardiac Bypass," 35, *Diseases of the Chest*, 554, (1959).
Heaney, "An Improved Technic [sic] for Vascular Isolation of the Liver: Experimental Study and Case Reports," 163, *Anals of Surgery*, 237, (1965).
Schrock, "Management of Blunt Trauma to the Liver and Hepatic Veins," 96, *Archives in Surgery*, 698, (1968).
Albo, "Massive Liver Trauma Involving the Suprarenal Vena Cava," 118, *The American Journal of Surgery*, 960, (1969).
Chavez-Peon, "Vena Cava Catheter for Asanguineous Liver Resection," 67, *Surgery*, 694, (1970).
Norman, "A Single Cannula for Aortic Perfusion and Left Ventricular Decompression," 58, *Chest*, 378, (1970).

List Continued on next page.

*Primary Examiner*—Stephen C. Pellegrino
*Attorney, Agent, or Firm*—Workman, Nydegger & Jensen

[57] ABSTRACT

A venous return catheter is provided having a first diameter distal portion suitable for insertion in a vena cava, a second, larger diameter proximal portion, and a transition portion forming a smooth transition between the first and second diameter portions. Drainage openings are provided in both the proximal and distal catheter portions. The catheter is of unitary construction, having a smooth bore through its entire length. It is also constructed from a soft, resilient material, but is reinforced with a harder, stiffer material in the region of the proximal drainage openings. The catheter may also be provided with wire reinforcement. The catheter is manufactured by a dip-molding process utilizing a male mandrel as a form.

16 Claims, 4 Drawing Figures

OTHER PUBLICATIONS

Kolff, "Transapical Left Ventricular Bypass," 103, Archives of Surgery, 656, (1971).

Bricker, "Surgical Management of Injuries to the Vena Cava: Changing Patterns of Injury and Newer Techniques of Repair," 11, The Journal of Trauma, 725, (1971).

Brown, "Temporary Internal Vascular Shunt for Retrohepatic Vena Cava Injury," 11, The Journal of Trauma, 736, (1971).

Morton, "The Treatment of Liver Injuries," 134, Surgery, Gynecology & Obstetrics, 298, (1972).

Sabisten, "Extracorporeal Circulation," Textbook of Surgery, 2112–13, (1972).

Brenner, "Nonthrombogenic Aortic and Vena Caval Bypass Using Heparin–Coated Tubes," 127, The American Journal of Surgery, 555, (1974).

Reed, "Cannulation," Cardiopulmonary Perfusion, 228, (1975).

Vidne, "Single-Stitch Fixation of Coronary Artery Perfusion Cannulas," 19, The Annals of Thoracic Surgery, 725, (1975).

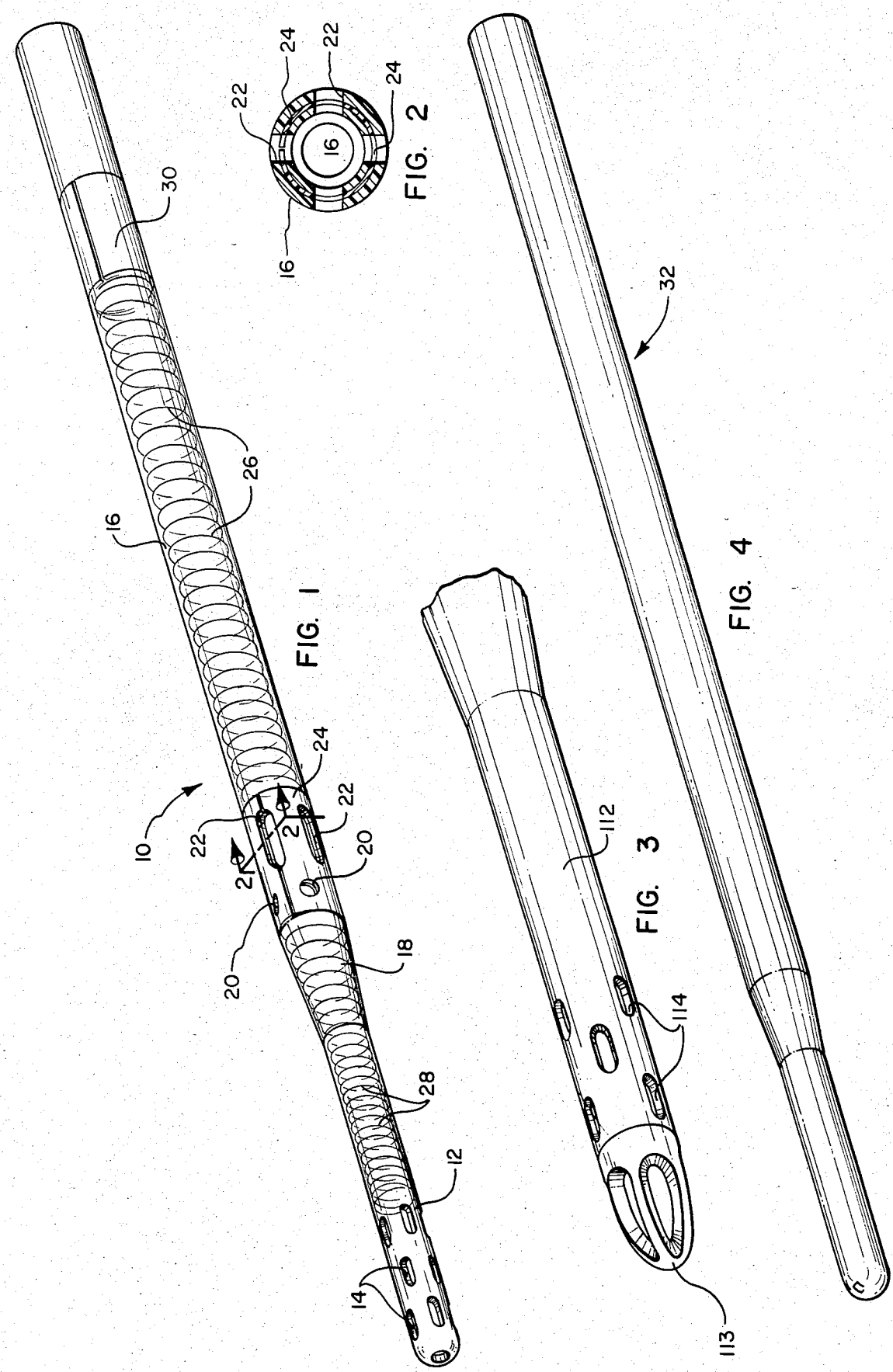

VENOUS RETURN CATHETER

BACKGROUND

1. The Field of the Invention

The present invention relates to catheters used in draining venous blood for treatment in extracorporeal life support equipment during surgical procedures requiring cardiopulmonary bypass. More particularly, the present invention is directed to a venous return catheter adapted for use in draining blood from the right atrium and the vena cavae.

2. The Prior Art

It is a routine requirement of a variety of surgical procedures to utilize extracorporeal cardiopulmonary bypass in order to mechanically perform the functions normally conducted by the heart and lungs. Venous blood depleted in oxygen and rich in carbon dioxide is mechanically removed from the patient and pumped to an oxygenating apparatus in order to oxygenate the blood and remove excess carbon dioxide. The blood is then returned to the patient's arterial system.

It is exceedingly important that adequate volumes of blood be drained from the patient during cardiopulmonary bypass so that the extracorporeal life support equipment can keep up with the patient's need for oxygen and can adequately remove excess carbon dioxide. Insufficient quantities of oxygen can lead to serious tissue damage. Inadequate removal of carbon dioxide leads to a condition known as "acidosis," which can result in serious consequences caused by the alternation in normal metabolic functioning of critical enzymes. Either condition can result in serious injury to the patient.

It will be appreciated that many factors affect the ability to drain adequate volumes of blood from a patient during cardiopulmonary bypass.

Two such factors are the design and placement techniques of drainage catheter used to remove the venous blood from the patient for extracorporeal treatment. Numerous catheter designs and placement techniques have been devised and tested, and various catheter designs and cannulation techniques have been recognized as safe and effective for venous drainage during cardiopulmonary bypass.

One such technique involves placement of a pair of catheters, one into the superior vena cava, and another into the inferior vena cava, in order to collect venous blood returned to the patient's right atrium. This technique is extremely reliable but suffers from the disadvantage that it takes time to surgically place two catheters, and then to suture the insertion locations when the catheters are removed following bypass. Nevertheless, because of problems experienced in connection with conventional single catheter designs discussed below, some physicians continue to utilize a two catheter technique.

A second general technique involves placement of a single catheter. Many physicians prefer a single catheter technique over a two catheter technique because only one incision is required, thereby simplifying and shortening the cannulation procedure both at the time of insertion and at the time of removal. It is also helpful to reduce the number of catheters that a surgeon must work around as he conducts surgery on the patient.

One variation of the single catheter technique involves placement of a catheter so that its distal tip lies in the right atrium. Such a placement permits the catheter to collect blood draining into the right atrium from the inferior vena cava and from the superior vena cava. While this procedure is capable of achieving adequate venous drainage, on occasion the catheter tip is overinserted or otherwise inadvertently manipulated so that the drainage openings in the catheter are pressed against tissue within the right atrium, thereby reducing or even interrupting blood flow into the catheter. This can be extremely dangerous to the patient. Because of these dangers, only a relatively small number of physicians utilize this procedure.

A second variation of the single catheter technique is a hybrid of the two catheter and single catheter techniques described above. Thus, a single catheter is provided having drainage openings not only at the distal end, but also along its length proximal to the distal end. Such a catheter, sometimes referred to as a "dual drainage" catheter, is then inserted through the right atrium and into either the inferior vena cava or the superior vena cava, with the proximal drainage openings positioned within the right atrium. This placement permits blood to be drained simultaneously from the vena cava in which the dual drainage catheter is placed and from the right atrium.

Due to the presence of multple drainage openings along a portion of the length of a dual drainage catheter, blood flow is less likely to become dangerously reduced when utilizing this type of catheter than when utilizing a simple single catheter. However, conventional dual drainage catheter designs still suffer form some significant disadvantages.

Commonly, conventional dual drainage catheters have a multi-diameter structure, with a relatively small diameter distal catheter portion (e.g., 36 French) and a larger diameter proximal portion (e.g., 51 French). Such catheters are typically constructed by forming a molded reducer having elongate slots therein, and then affixing suitable lengths of 36 French and 51 French tubing to opposite sides of the reducer.

Optimally, the distal portion of the catheter is inserted only partially into one of the vena cavae so that the proximal drainage openings remain substantially centered within the right atrium. Sometimes, however, the catheter is overinserted, occasionally so much so that the proximal drainage openings are partially occluded at the entrance to the vena cava, or are actually inserted into the vena cava so that both distal and proximal drainage openings drain from the vena cava, and none drain the right atrium. This results in a substantial reduction in venous drainage.

The conventional dual drainage catheter formed form two lengths of tubing and a molded reducer member also suffers from other disadvantages. For example, the blood flow pathway is interrupted at the two positions where the catheter tubing is connected to the molded reducer. This tends to cause turbulence at these two positions, which in turn can cause damage to red blood cells, and can initiate a clotting reaction.

Yet a further disadvantage when using a reducer and attached tubing is the possibility that one of the tubes will become separated from the reducer during use. Such a separation during bypass could easily result in serious injury to the patient.

Additionally, the use of a molded reducer tends to inflict tissue damage as the reducer is inserted into the right atrium. This is because blood is returned from the patient's venous system to the right atrium under pressure, so that the incision through which the catheter is inserted must be kept tightly closed around the catheter or a significant volume of blood will leak out. As the small diameter leading portion of the catheter is inserted, a clamp is used to hold the heart tissue tightly against the catheter so as to prevent blood leakage. As the catheter continues to be inserted, the reducer eventually comes in contact with the clamped tissue. As noted above, this reducer is unyielding, and has a number of still ridges increasing in diameter from the distal to proximal end that form the drainage openings. As this unyielding reducer is forced through the incision, it is not uncommon to inflict tissue damage. There is also a tendency for tissue to drag or catch on the reducer drainage openings, thereby causing yet additional tissue damage. Even when no damage to tissue results, this tendency of the catheter to "hang up" as it is inserted is a source of irritation to the surgeon and causes him to lose concentration.

Another common difficulty is inherent in the most common dual drainage catheter placement technique. Most often, a dual drainage catheter is used by inserting it through the right atrial appendage and then into the inferior vena cava. Since the inferior vena cava is not directly opposite the right atrial appendage, placement of a catheter using this conventional placement technique results in a bend of about 30 degrees in the distal portion of the catheter.

Normally, this causes no problems. Some surgical procedures, however, require manipulation or movement of the heart. Since the inferior vena cava is substantially anchored in place, manipulation of the heart frequently increases the angle of bend in the portion of the catheter situated at the juncture between the inferior vena cava and the right atrium. Not uncommonly the increased degree of bending causes the catheter to become kinked. This, of course, restricts or even interrupts blood drainage from the inferior vena cava, and hence reduces overall blood drainage.

In veiw of the foregoing it will be appreciated that it would be a substantial contribution in the field of venous return catheters if an improved single venous return catheter could be provided that successfully avoided the aforementioned problems. The present invention provides such an improved catheter.

PRINCIPLE OBJECTS AND BRIEF SUMMARY OF THE INVENTION

In view of the foregoing problems experienced with conventional single venous return catheters, it is a primary object of the present invention to provide an improved venous return catheter capable of use as a single catheter for venous drainage that avoids the tendency for its drainage openings to become wholly or partially blocked when inserted, thereby ensuring adequate blood drainage.

It is another primary object of the present invention to provide an improved venous return catheter that is less likely to become kinked during use.

Yet another principal object of the present invention is to provide a venous return catheter that is relatively resilient so as to avoid or minimize tissue irritation during placement and use.

Still a further important object of the present invention is to provide a unitary one-piece venous return catheter having a smooth bore that will minimize the extent of hemolysis as blood is drained therethrough and that will retain its integrity during use.

Yet a further important object of the present invention is to provide a process for manufacturing a catheter having the above-identified features.

These, and other, objects and features of the present invention will become more fully apparent from the following description and appended claims taken in conjunction with the accompanying drawings.

In accordance with the foregoing principal objects, the present invention is directed to a novel dual drainage venous return catheter and a method for manufacturing such a catheter.

A presently preferred embodiment of a venous return catheter constructed in accordance with the present invention includes a first diameter distal portion capable of placement within a vena cava, and a larger diameter proximal portion interconnected to the smaller diameter portion through a smoothly tapered transition portion. Drainage openings are provided in both the proximal and distal catheter portions. The catheter is of unitary construction so that it has a smooth bore and lacks junctions which can contribute to hemolysis. Advantageously, the catheter is constructed from a resilient material to minimize tissue damage during insertion and removal. The catheter may optionally be provided with wire reinforcement to prevent kinking, and is advantageously reinforced in the area of the drainage openings.

Catheters in accordance with the present invention are advantageously manufactured by providing a mandrel having the dimensions of the desired catheter bore. Using a dipmolding technique, the unitary catheter and reinforcing materials are then formed around the mandrel.

BRIEF DESCRIPTION OF THE DRAWINGS

In the accompanying drawings, which represent the best mode presently contemplated for carrying out the invention:

FIG. 1 is a perspective view of a presently preferred embodiment of a dual drainage venous return catheter in accordance with the present invention.

FIG. 2 is a transverse sectional view of the catheter of FIG. 1 taken along line 2—2 of FIG. 1, and drawn to a larger scale.

FIG. 3 is a perspective view of the distal end portion of another presently preferred embodiment of venous return catheter, having an alternative distal drainage arrangement, and drawn to a larger scale.

FIG. 4 is a perspective view of a mandrel suitable for use in fabricating a venous return catheter in accordance with the present invention.

DETAILED DESCRIPTION OF THE PRESENTLY PREFERRED EMBODIMENTS OF THE INVENTION

The present invention can best be understood by a detailed reference to the drawings, in which like parts are designated with like numerals throughout.

FIG. 1 illustrates a presently preferred embodiment 10 of a venous return catheter in accordance with the present invention. As seen in FIG. 1, catheter 10 has three separately identifiable portions.

A distal portion 12 of the catheter has a first diameter suitable for insertion into one of the vena cavae of a patient. Distal portion 12 need not fit tightly within the vena cavae, but neither should it be unduly small since blood flow becomes restricted as the diameter of the catheter is decreased. In order to accommodate a variety of patients without a large number of different sizes of catheters, it is anticipated that a typical catheter in accordance with the present invention intended for use with adults will have a distal portion outside diameter of about 12 millimeters and an inside diameter of about 9 to 10 millimeters. Nevertheless, it will be appreciated that the distal portion of catheter 10 may have a larger or smaller diameter without departing from the present invention.

Distal portion 12 of catheter 10 is provided with drainage openings 14 in order to effect blood drainage from the vena cava in which it is inserted. It is preferable to provide multiple drainage openings to ensure adequate drainage and to minimize the chance that blood flow will be significantly impeded should a portion of the catheter become occluded by the wall of the vena cava. In order to appreciate the wide latitude possible in designing suitable drainage openings, FIG. 3 illustrates an alternative embodiment of a distal catheter portion 112 fitted with a modled tip 113 and further provided with optional drainage openings 114. It will be appreciated that numerous other variations effective for achieving adequate drainage are possible.

Returning to a consideration of FIG. 1, it will be seen that in addition to a distal portion 12, catheter 10 also has a proximal portion 16. Proximal portion 16 preferably has a larger diameter than does the distal portion of catheter 10, in order to accommodate the increased volume of blood drained from the right atrium in addition to that passing therethrough from the distal portion. It is anticipated that proximal portion 16 of catheter 10 intended for adult use will have an outside diameter of about 17 millimeters, and an inside diameter of about 14 to 15 millimeters.

The proximal and distal portions 12 and 16 catheter 10 are advantageously interconnected by a transition portion 18.

In the past, one approach to constructing a dual drainage catheter has been to connect tubing of two different diameters to a molded reducer. Such a reducer included a number of elongate slots to permit blood drainage from the right atrium into the tubing connected to the proximal side of the reducer. Even subsequent catheter designs of one-piece construction have maintained drainage holes in the region of transition.

The venous return catheter of the present invention departs from this longstanding practice and provides drainage openings 20 and 22 in the proximal portion of the catheter rather than in the transition portion. This arrangement avoids the risk that the catheter will be overinserted to the point where drainage openings in the transition portion could become occluded by tissue at the entrance to the vena cava. Even partial insertion of proximal catheter portion 16 into the vena cava will leave some drainage openings 20 and 22 exposed to the right atrium.

Additionally, conventional catheter designs tend to snag or catch on patient tissue around the incision through which they are inserted. This is because a surgeon placing a dual drainage catheter uses a purse-string suture to hold the tissue tightly around the catheter so as to prevent blood leakage. While not acute, the problem of snagging tissue is irritating to the surgeon and can cause additional trauma to the patient's tissue. Moving the drainage openings onto the proximal diameter portion and off of the transition portion substantially avoids this problem.

Catheter 10 is illustrated as having two different shapes and sizes of proximal drainage openings 20 and 22. It should be understood that this arrangement is not necessary, and any suitable openings capable of draining blood from the right atrium may be employed without departing from the teachings of the present invention.

In the presently preferred embodiment of catheter 10 illustrated in FIG. 1, it will be observed that proximal drainage openings 20 and 22 are situated fairly near to transition portion 18. This arrangement is useful when catheter 10 is constructed with dimensions similar to conventional catheters, because it ensures effective placement of the proximal drainage openings so as to drain blood from the right atrium.

Such a placement is not necessary however. An important feature of the present invention is the flexibility available. As noted above, one disadvantage of conventional catheter designs is the ability of a surgeon to incorrectly place the catheter where it will effect optimum venous drainage. A catheter in accordance with the present invention could easily overcome this problem by providing a proximal catheter portion 16 having a diameter too large to be inserted into the vena cavae. In use, such a catheter could advantageously be inserted to the point where it comes to rest against the vena cava. Drainage openings could then be situated at an appropriate location along the length of proximal catheter portion 16 so as to effect desired drainage from the right atrium. (In the past, it has been common to place a dual drainage catheter so that the proximal drainage openings are situated in the center of the right atrium).

It is preferred that catheter 10 be constructed from a somewhat soft, flexible material so as to minimize tissue damage during insertion and use. Use of a soft material, however, can result in kinking at the location of the proximal drainage openings.

Accordingly, it has been found desirable to add reinforcement by means of a reinforcing member 24 at the location of the proximal drainage openings 20 and 22. This reinforcing member is advantageously of a harder, stiffer material than the rest of the catheter. As best seen in FIG. 2, reinforcing member 24 is preferably incorporated within the body of proximal portion 16.

Kinking is also a problem in other areas of the catheter when performing certain surgical procedures. Wire reinforcement has long been utilized within the proximal portion of a dual drainage catheter. Such a reinforcing wire member 26 may advantageously be provided in catheter 10.

However, the most severe problems of kinking are more likely to occur in the distal portion of the catheter near the location where it enters the vena cava. Certain surgical procedures require that a patient's heart be rotated or otherwise manipulated. Yet, the inferior vena cava is substantially anchored in place by surrounding anatomical features. When a dual drainage catheter is placed in the inferior vena cava, manipulation of the heart causes movement of the proximal portion of the catheter, but the distal portion placed in the inferior vena cava remains substantially unmoved. This frequently results in kinking in the distal catheter portion.

To prevent this problem, a venous return catheter in accordance with the present invention may optionally be provided with a wire member 28 capable of reinforcing the distal and transition catheter portions. Advantageously, wire member 28 extends from reinforcing member 24, through transition portion 18, and sufficiently along distal portion 12 so that the portion of catheter 10 near the junction between the vena cava and the right atrium will be wire reinforced. Such use of wire member 28 leaves the catheter flexible but virtually eliminates kinking problems in the distal catheter portion.

Catheter 10, of course, is intended to be connected to an extracorporeal life support system. In order to facilitate connection of the proximal end of catheter 10 to tubing draining into an extracorporeal life support system, wire member 26 is terminated short of the proximal end of the catheter. Further, wire member 26 must terminate sufficiently short to permit the catheter to be clamped so as to prevent leakage before it is connected to the extracorporeal life support system.

Unfortunately, following attachment of the catheter to the extracorporeal life support system, the unreinforced area where the catheter was clamped provides a likely site in an otherwise reinforced catheter where kinking can occur. Accordingly, in catheters provided with wire member 26, it is advantageous to further provide a second reinforcing member 30 similar to reinforcing member 24. The catheter can be clamped at reinforcing member 30 so as to prevent leakage, and tubing from the extracorporeal system can be inserted to the edge of reinforcing member 30, leaving no portion of catheter unreinforced.

Catheter 10 may advantageously be constructed by a dipmolding process. In order to use this process a mandrel 32 is prepared having dimensions corresponding to the desired internal dimensions of the catheter. It is possible to construct a mandrel to exacting specifications, and also having a very smooth transition between the differing diameter proximal and distal portions. This will result in a unitary catheter having a very smooth bore that will minimize the possibility of damaging delicate blood cells passing therethrough.

The mandrel is initially preheated to a temperature capable of effecting partial curing of the material from which the catheter is to be constructed. The mandrel is then dipped into a container of liquid, uncured material and left until a suitable thickness of material gels and adheres to the mandrel.

It is quite possible to cure the material at that stage and provide a catheter needing only the addition of drainage holes to be effective. However, it is preferable to remove the madrel while it only has a very thin layer of material, and then partially cure that layer. Reinforcement members 24 and 30 and wire members 26 and 28 may then be added over the initial layer. The mandrel is then reheated and dipped a second time to form material around and over the wire and reinforcement material. The catheter is then cured, removed from the mandrel, and drainage holes added.

The manufacturing process will be better appreciated by reference to an illustrative example:

EXAMPLE I

As noted above, an important feature of the present invention is that a catheter can be constructed from a very soft, resilient material. Thus, a vat is provided at room temperature of uncured polyvinylchloride material sold under the name Plastisol, having a 50 Shore A durometer hardness.

A suitable mandrel 32 is then preheated to about 500° F. and dipped into the vat of Plastisol for about 15 to 20 seconds, resulting in an initial layer of partially cured material about ¾ millimeters thick.

Next, the mandrel is removed from the vat and placed in an oven at about 500° F. for about two minutes so that the Plastisol will become about 50 percent cured. This gives the Plastisol sufficient body to retain its form, but leaves it still tacky.

A stainless steel wire preformed into a helical coils approximately the same diameter as the partially formed catheter is next slipped into place, and strips of reinforcing material are wrapped around the mandrel at locations corresponding to that illustrated in FIG. 1. The reinforcing material is harder and stiffer than the Plastisol used for the body of the catheter. Advantageously, a 90 Shore A durometer polyvinylchloride material (called "Ridigsol") having a thickness of about one millimeter is used for this purpose.

The mandrel is then reheated to about 500° F., and dipped a second time into the vat of Plastisol. This time the mandrel is left suspended in the Plastisol for about 90 seconds while a second layer of Plastisol forms over the wire and the reinforcing material and underlying Plastisol layer.

The mandrel is then returned to the curing oven and the catheter is fully cured. The result is a unitary one-piece catheter having wire and structural reinforcement encapsulated therein at critical areas.

Finally, the catheter is removed from the mandrel, trimmed to size, and drainage holes are punched therein. It is then ready to be packaged and sterilized for use.

It will be appreciated from the foregoing that the present invention provides a venous return catheter that is significantly improved over conventional catheters.

Thus, unlike conventional dual drainage catheters, the provision of drainage holes proximal to the transition portion of the catheter avoids the likelihood that those drainage holes will be occluded due to overinsertion of the catheter. Further, since the drainage openings are not restricted to a relatively small area on the transition portion, it is possible to locate the holes at any convenient place along the catheter, and to use any convenient number, variety, and size of openings that may be desirable for a particular application.

Provision of a unitary one-piece catheter having a smooth bore minimizes hemolysis during blood drainage. In contrast, conventional designs incorporating a molded reducer to which two lengths of tubing are affixed have abrupt junctures which can contribute to hemolysis. A unitary catheter also avoids the risk inherent in a multi-piece catheter that the catheter will separate during use.

Being advantageously constructed from a soft, resilient material, the catheter of the present invention is also less harmful to tissue than is a conventional catheter. Despite this softness, use of reinforcement members and wire reinforcement prevents kinking in the catheter, even at the juncture of the right atrium and the vena cava.

Hence, the present invention is a significant contribution to the art of venous return catheters. Its use can improve the likelihood that venous drainage will be adequate during surgical procedures requiring cardiopulmonary bypass, and will minimize trauma to patient tissues with which it comes in contact, or blood hemolysis.

Although the apparatus of the present invention has been shown and described in reference to particular embodiments, it is to be understood that the apparatus of the invention may also be embodied in other specific forms without departing from its spirit or essential characteristics. The described embodiments are to be considered in all respects only as illustrative, and not restrictive. The scope of the invention is, therefore, indicated by the appended claims rather than by the foregoing description. All changes which come within the meaning and range of equivalency are to be embraced within their scope.

What is claimed and desired to be secured by United States Letters Patent is:

1. A catheter for use in the venous drainage of blood during surgical procedures involving cardiopulmonary bypass, comprising:

a first diameter catheter portion forming the distal end of the catheter, said first diameter portion being suitable for placement within a vena cava, and said first diameter portion being provided with a plurality of drainage openings suitable for draining blood;

a second diameter catheter portion forming the proximal end of said catheter, said second diameter portion being in fluid communication with the first diameter portion, said second diameter catheter portion having a larger diameter than the first diameter portion, said second diameter portion being provided with drainage openings suitable for draining blood, and further being provided with reinforcement means for reinforcing a section of the second diameter catheter portion surrounding the drainage openings, the reinforcement means comprising a substantially continuous layer of a reinforcing material, the drainage openings being punched through said layer of reinforcing material; and a transistion catheter portion between the first and second diameter portions forming a smooth transition between said first and second diameter portions.

2. A venous return catheter as defined in claim 1, wherein said catheter is of unitary one-piece construction and having a smooth bore.

3. A venous return catheter as defined in claim 2, wherein said catheter is formed from a relatively soft material.

4. A venous return catheter as defined in claim 3, further comprising coiled wire reinforcement secured within the body of said catheter.

5. A venous return catheter as defined in claim 4, wherein the wire reinforcement is provided substantially along the length of the catheter except where the respective drainage openings and reinforcement means are provided.

6. A venous return catheter as defined in claim 5, wherein the wire reinforcement terminates sufficiently short of the proximal end of the catheter so as to permit said proximal end to be clamped during insertion of the catheter and connected to an extracorporeal bypass system.

7. A venous return catheter as defined in claim 1, wherein the area of said catheter which is to be clamped is provided with reinforcement means comprising a substantially continuous layer of a reinforcement material.

8. A venous return catheter as defined in claim 1, wherein the second diameter portion has a diameter sufficiently large that said second diameter portion will not readily enter into the vena cava, and wherein the drainage openings in the second diameter portion are situated so as to be substantially centered in the right atrium when the catheter is inserted fully into the vena cava.

9. A catheter for use in the venous drainage of blood during surgical procedures involving cardiopulmonary bypass, comprising:

a first diameter catheter portion forming the distal end of the catheter, said first diameter portion being suitable for placement within a vena cava, and said first diameter portion being provided with a plurality of drainage openings suitable for draining blood;

a second diameter catheter portion forming the proximal end of said catheter, said second diameter portion being in fluid communication with the first diameter portion and having a diameter sufficiently large that said second diameter portion will not readily enter into the vena cava, said second diameter portion being provided with drainage openings suitable for draining blood, and further being provided with reinforcement means for reinforcing a section of the second diameter catheter portion surrounding the drainage openings, the reinforcement means comprising a substantially continuous layer of a reinforcing material, the drainage openings being punched through said layer of reinforcing material; and a transition catheter portion between the first and second diameter portions forming a smooth transition between said first and second diameter portions.

10. A venous return catheter as defined in claim 9, wherein said catheter is of unitary one-piece construction and having a smooth bore.

11. A venous return catheter as defined in claim 10, wherein said catheter is formed from a relatively soft material.

12. A venous return catheter as defined in claim 11, further comprising coiled wire reinforcement secured within the body of said catheter.

13. A venous return catheter as defined in claim 12, wherein the wire reinforcement is provided substantailly along the length of the catheter except where the respective drainage openings and reinforcement means are provided.

14. A venous return catheter as defined in claim 13, wherein the wire reinforcement terminates sufficiently short of the proximal end of the catheter so as to permit said proximal end to be clamped during insertion of the catheter and connected to an extracorporeal bypass system.

15. A venous return catheter as defined in claim 14, wherein the area of said catheter which is to be clamped is provided with reinforcment means comprising a substantially continuous layer of a reinforcement material.

16. A venous return catheter as defined in claim 9, wherein the drainage openings in the second diameter portion are situated so as to be substantially centered in the right atrium when the catheter is fully inserted into the vena cava.

* * * * *